United States Patent
Reyneke et al.

(10) Patent No.: US 12,258,313 B2
(45) Date of Patent: Mar. 25, 2025

(54) THERMALLY COUPLED DISTILLATION SCHEME FOR PURIFICATION OF CUMENE

(71) Applicant: Kellogg Brown & Root LLC, Houston, TX (US)

(72) Inventors: Rian Reyneke, Katy, TX (US); Eric Wing-Tak Wong, Houston, TX (US)

(73) Assignee: KELLOGG BROWN & ROOT LLC, Houston, TX (US)

( * ) Notice: Subject to any disclaimer, the term of this patent is extended or adjusted under 35 U.S.C. 154(b) by 0 days.

(21) Appl. No.: 18/078,036

(22) Filed: Dec. 8, 2022

(65) Prior Publication Data

US 2023/0183153 A1 Jun. 15, 2023

Related U.S. Application Data

(60) Provisional application No. 63/288,376, filed on Dec. 10, 2021.

(51) Int. Cl.
  *C07C 7/05* (2006.01)
(52) U.S. Cl.
  CPC ...................................... *C07C 7/05* (2013.01)
(58) Field of Classification Search
  CPC ..................... C07C 7/05; C07C 7/04
  See application file for complete search history.

(56) References Cited

U.S. PATENT DOCUMENTS

| | | | |
|---|---|---|---|
| 4,555,311 | A | 11/1985 | Ward |
| 5,847,253 | A | 12/1998 | Ho et al. |
| 6,096,035 | A | 8/2000 | Sodhi et al. |
| 2011/0245558 | A1 | 10/2011 | Schmidt |
| 2019/0169094 | A1 | 6/2019 | Kim et al. |

OTHER PUBLICATIONS

Patent Cooperation Treaty, International Search Report and Written Opinion of the International Searching Authority; International Application No. PCT/US22/52321 filed Dec. 8, 2022; 6 pages.

*Primary Examiner* — Thuan D Dang
(74) *Attorney, Agent, or Firm* — Gary M. Machetta

(57) ABSTRACT

A method for purifying cumene may include splitting an alkylation reaction product into a first portion and a second portion; feeding the first portion as mostly a liquid into a benzene column; at least partially vaporizing the second portion in a heater; feeding the at least partially vaporized second portion into the benzene column. A method for purifying cumene may also include the steps of providing a benzene column and a cumene column; directing a liquid side draw from the benzene column to the cumene column, the liquid side draw being a liquid substantially free of DIPB; returning a benzene enriched vapor from the cumene column to the benzene column using an overhead line, the benzene enriched vapor having a higher concentration of benzene than the liquid side draw; and drawing purified cumene from the cumene column.

9 Claims, 2 Drawing Sheets

THERMALLY COUPLED DISTILLATION SCHEME FOR PURIFICATION OF CUMENE

CROSS-REFERENCE TO RELATED APPLICATIONS

This application takes priority from U.S. Provisional Patent Application Ser. No. 63/288,376 filed Dec. 10, 2021, the contents of which are incorporated by reference for all purposes.

BACKGROUND

Field

Embodiments described herein generally relate to methods and systems for purification of cumene.

Description of the Related Art cumene is commercially produced through an alkylation reaction of benzene (in surplus) with propylene. The reactor effluent contains a significant amount of benzene along with minor light components, as well as heavies primarily consisting of diisopropylbenzene (DIPB) along with other minor heavy by-products. After fractionation, DIPB is typically reacted with benzene in a transalkylation reactor to produce more cumene. In a conventional process, the effluents from the main alkylation reactor and transalkylation reactor feed to a benzene column to separate benzene from cumene through conventional distillation, followed by a cumene column to separate cumene from DIPB, also through conventional distillation.

FIG. 1 illustrates a conventional prior art arrangement 10 includes a benzene column 12 and a cumene column 14. The benzene column 12 receives a first feed 16 from an alkylation reactor and a second feed 18 from a transalkylation reactor. The benzene column 12 uses a direct separation sequence to first remove benzene as overhead product. The bottoms 20 of the benzene column 12 is directed to the cumene column 14, in which a separation of cumene and DIPB is performed. The benzene and cumene column fractionation steps are energy intensive and their reboilers consume approximately 90% of the total high-pressure steam (HPS, typically at around 40 barg) consumed in the cumene process.

FIG. 2 illustrates another prior art arrangement 30 that includes a fractionating column 32 that uses a single dividing wall 34, or collectively DWC 32. The DWC 32 receives a first feed 16 from an alkylation reactor and a second feed 18 from a transalkylation reactor and performs a three-way separation of benzene, cumene and DIPB. A configuration with optional side condenser 34 is shown. It has also been proposed to use a single dividing wall column to achieve the three-way separation as proposed in patent literature by UOP (WO 2008/147638 A1) or RRT. It is known in the art that the use of a DWC 32 in certain applications can reduce total heat input to a distillation process as compared to the FIG. 1 arrangement.

While the use of dividing wall columns to achieve a three-way separation is well known in the art, industry has been slow to adopt these designs due to the reduced operational flexibility and the additional design challenges that it poses. The teachings of the present disclosure can substantially reduce the HPS consumption of the process without using a DWC.°

SUMMARY OF THE DISCLOSURE

In aspects, the present disclosure provides a method for purifying cumene. The method may include splitting an alkylation reaction product into a first portion and a second portion; feeding the first portion as mostly a liquid into a benzene column, the benzene column being configured to separate at least benzene from the alkylation reaction product; at least partially vaporizing the second portion in a heater; feeding the at least partially vaporized second portion into the benzene column; and separating at least benzene from the alkylation reaction product in the benzene column.

In further aspects, the present disclosure provides a system for purifying cumene. The system may include a split feed assembly configured to receive an alkylation reaction product via an alkylation feed line, wherein the split feed assembly is configured to form the alkylation reaction product into a mostly liquid first portion, and wherein the split feed assembly includes a heater configured to least partially vaporize the second portion to form an at least partially vapor second portion; and a benzene column configured to separate at least benzene from the mostly liquid first portion and the at least partially vapor second portion.

In still further aspects, the present disclosure provides a method for purifying cumene. The method may include providing a benzene column and a cumene column; directing a liquid side draw from the benzene column to the cumene column, the liquid side draw being a liquid substantially free of DIPB, the liquid side draw acting as a reflux to the cumene column; returning a benzene enriched vapor from the cumene column to the benzene column using an overhead line, wherein the benzene enriched vapor has a higher concentration of benzene than the liquid side draw; and drawing a purified cumene from the cumene column.

In still further aspects, the present disclosure provides a system for purifying cumene. The system may include a benzene column and a cumene column; a liquid side draw configured to direct a liquid substantially free of DIPB from the benzene column to the cumene column, the directed liquid being a reflux to the cumene column; an overhead line from the cumene column configured to return a benzene enriched vapor to the benzene column, wherein the benzene enriched vapor has a higher concentration of benzene than the drawn liquid; and a product side draw configured to draw the purified cumene from the cumene column.

The above-recited examples of features of the disclosure have been summarized rather broadly in order that the detailed description thereof that follows may be better understood, and in order that the contributions to the art may be appreciated. There are, of course, additional features of the disclosure that will be described hereinafter and which will form the subject of the claims appended hereto.

BRIEF DESCRIPTION OF THE DRAWINGS

For detailed understanding of the present disclosure, references should be made to the following detailed description of the preferred embodiment, taken in conjunction with the accompanying drawings, in which like elements have been given like numerals and wherein.

DETAILED DESCRIPTION

Figure 1:
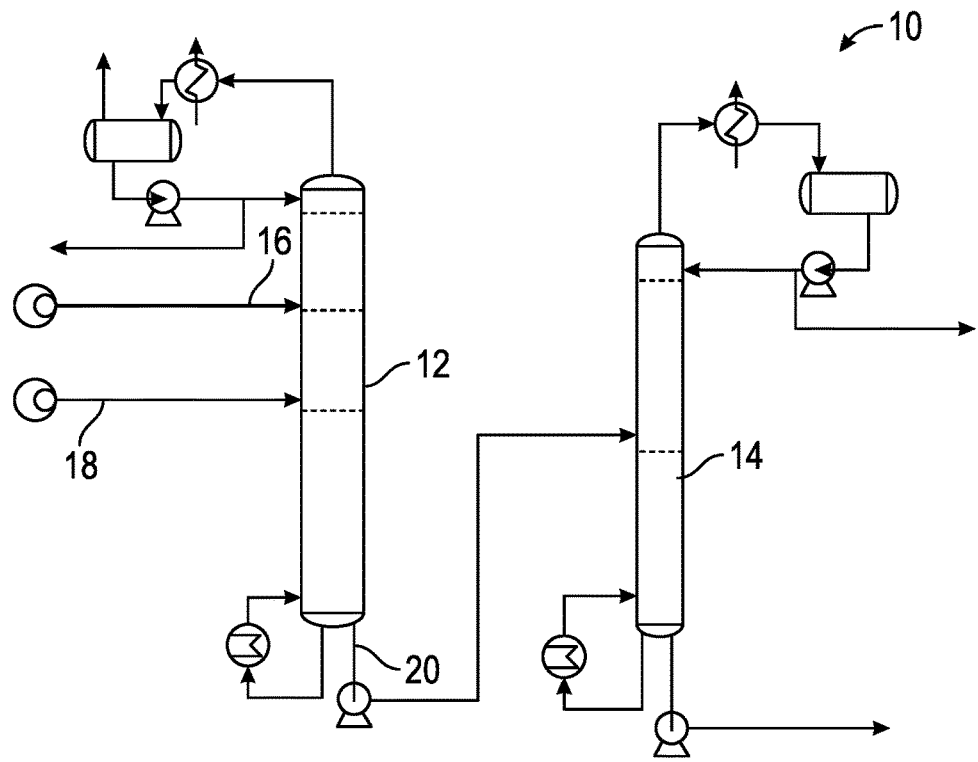
FIGS. 1 and 2 depict prior art cumene distillation systems.
Figure 2:
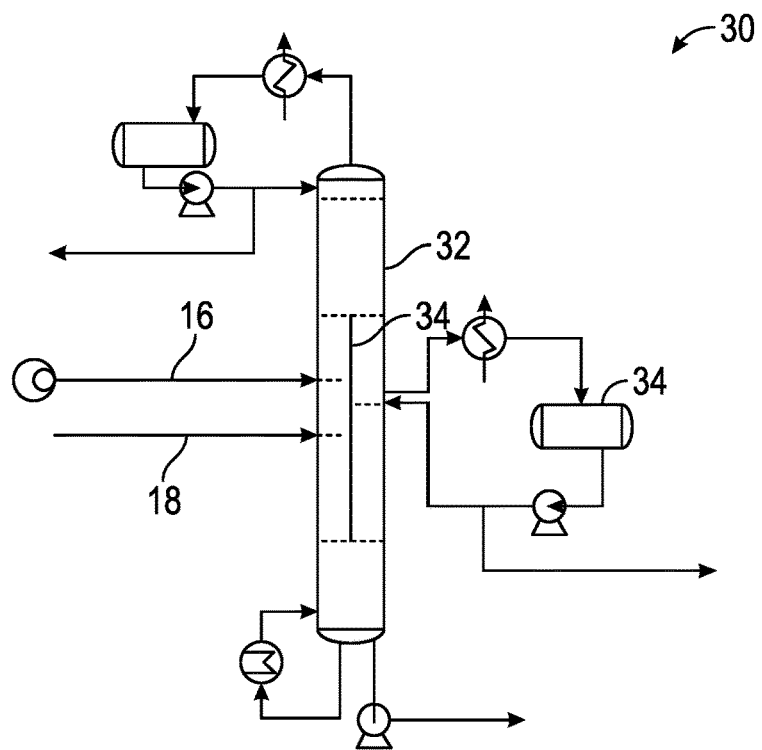

The present disclosure provides methods and related systems for substantially reducing energy consumption during a cumene distillation process. Equipment such as reboilers consume a relatively large amount of energy to maintain a specified temperature inside a column during operation. Often, the reboilers receive this energy in the form of high-pressure steam (HPS). In aspects, the present teachings can reduce the amount of energy consumed by a reboiler to maintain a specified process temperature, which then reduces the required thermal energy input to the reboiler whether the thermal energy is HPS or provided by other equipment such as a fired heater. The present disclosure is susceptible to embodiments of different forms. Embodiments of the present disclosure condition the alkylation feed and/or thermally couple the benzene column with the cumene column to reduce HPS consumption when compared to conventional prior art arrangements such as shown in FIGS. 1 and 2. Whether used with one another, or independently, feed conditioning and thermal coupling still obtain a reduction in HPS consumption vis-à-vis prior art arrangements. There are shown in the drawings, and herein will be described in detail, specific embodiments of the present disclosure with the understanding that the present disclosure is to be considered an exemplification of the principles of the disclosure and is not intended to limit the disclosure to that illustrated and described herein.

Figure 3:
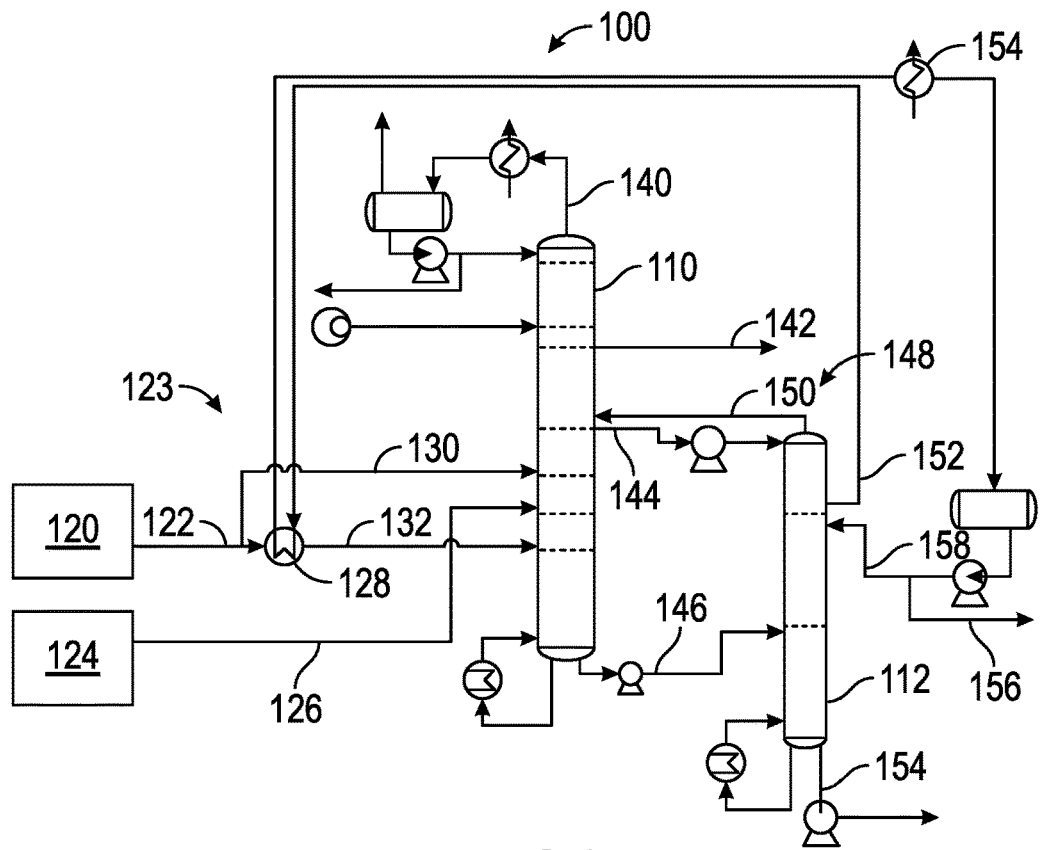
FIG. 3 depicts a system for producing cumene according to one embodiment of the present disclosure.

Referring to FIG. 3, there is shown a cumene distillation system 100, hereafter 'system 100,' according to one embodiment of the present disclosure for separating benzene, cumene and DIPB as major products by processing one or more alkylation feeds. In the illustrated embodiment, the system 100 processes alkylation and transalkylation feeds from an alkylation reactor 120 and a transalkylation reactor 124.

The alkylation reactor 120 is configured to alkylate benzene with propylene to form isopropylbenzene or cumene. Some polyisopropyl benzenes, which are mainly di- and tri-substituted propylbenzenes, may also be formed. benzene may be fed to the alkylator reactor 120 in excess so that virtually all the propylene is reacted. The effluent of the alkylation reactor 120, a first feed 122, contains primarily benzene, cumene and polyisopropyl benzenes. Optionally, the transalkylation reactor 124 may be configured to transalkylate the polyisopropyl benzene produced in the alkylation reactor 120. The effluent of the transalkylation reactor 124, a second feed 126, contains primarily benzene, cumene, and polyisopropyl benzene.

In one non-limiting embodiment, the system 100 may include a benzene column 110 configured to separate at least benzene from an alkylation reaction product and a cumene column 112 configured to separate at least cumene from feeds received from the benzene column 110. The columns 110, 112 may utilize a conventional configuration of a shell, one or more fractionating internals to promote contact among the various components inside the shell (e.g., trays or packing), and heat transfer equipment that consume energy, such as a reboiler and condensers. As noted previously, these energy consumers may use HPS or other forms of thermal energy input.

The benzene column 110 receives the first feed 122 from the alkylation reactor 120 and the second feed 126 from the transalkylation reactor 124. To reduce HPS consumption, the system 100 includes a split-feed assembly 123 formed of suitable flow lines. In one embodiment, the split-feed assembly 123 may include a heater 128 to condition the first feed 122. In this embodiment, split-feed assembly 123 splits the first feed 122 into a first portion 130 and a second portion 132. The first portion 130 enters the benzene column 110 at an upper feed location as mostly liquid, effectively acting similar to a reflux inside the benzene column 110. The second portion 132 passes through and is at least partially vaporized in the heater 128 and enters the benzene column 110 at a feed location below the first portion 130. In some embodiments, the second portion 132 is mostly a vapor. The preheating of the second portion 132 helps to reduce the reboiler duty due to the added heat content received at the heater 128.

In some embodiments, the transalkylation reaction product in feed 126 is fed into the benzene column 110 at a location between a first location at which the mostly liquid first portion 130 is fed into the benzene column 110 and a second location at which the at least partially vapor second portion 132 is fed into the benzene column 110. In non-limiting arrangements, the first feed 122 may be supplied in a temperature range of 110° C. and 160° C. The first portion 130 may enter the benzene column 110 in a temperature range between 110° C. and 130° C. After passing through the heater 128, the second portion 132 may enter the benzene column 110 in a temperature range of 120° C. and 170° C. The heater 128 may receive cumene vapor in a temperature range of 155° C. and 175° C. and the cumene vapor may exit the heater 128 in a temperature range of 145° C. and 165° C. It should be noted that these temperatures are merely illustrative and do not limit the temperature ranges at which the present teachings may be applied. Furthermore, merely for clarity, flow control devices such as let down valves are not shown but may be employed where appropriate.

As will be described below, the heater 128 receives thermal energy from cumene drawn from the cumene column 112. The heater 128 may be an indirect heater such as a heat exchanger or preheater. However, in other embodiments, the heater 128 may receive thermal energy from a difference source. As used throughout "mostly" means a majority; e, g., mostly liquid means more than fifty percent of a fluid is liquid.

The benzene column 110 has several effluents, including a benzene overhead 140, a benzene product side draw 142, a cumene side draw 144, and a bottoms stream 146. The fluid in the benzene product side draw 142 includes benzene purified to a predetermined benzene product concentration specifications. The cumene side draw 144 is taken from the upper part of the benzene column 110 and fed to the cumene column 112. The side draw 144 is a mostly cumene liquid that is substantially free of diisoPropylbenzene (DIPB). Herein, "substantially free of DIPB" means the DIPB concentration is below a predefined concentration level in the purified cumene product. In embodiments, DIPB content less than wt 100 ppm may be considered "substantially free of DIPB." The cumene side draw 144 acts as a reflux to the cumene column 112. The bottoms stream 146, which is substantially free of benzene, is also fed to the cumene column 112. Herein, "substantially free of benzene" means the benzene concentration is below the concentration of benzene in the side draw 142. In embodiments. benzene content below 100 wt ppm may be considered "substantially free of benzene."

The cumene column 112 has several effluents, including a vapor overhead 150, a cumene product side draw 152, and a DIPB bottoms 154. The overhead vapor 150 is a benzene enriched cumene stream that returns to the same stage as the side draw 144 in the benzene column 110. The return location is generally between the benzene product side draw 142 and above the bottoms stream 146. The product-quality cumene side draw 152 is a vapor stream taken from the cumene column 112 and at least partially condensed in the heater 128 to provide feed preheat for the feed second portion 132 as described previously. The side draw 152 may also undergo a secondary cooling in a heat exchanger 154, which may be used for low pressure steam generation. The cooled side draw 152 may be condensed and split into a first portion 156 that leaves as condensed cumene product and a second portion 158 that returns to the cumene column 112 as reflux. The second portion 158 may be returned at location proximate to where the side draw 152 is taken from the benzene column 110.

It should be appreciated that the side draw 144 and the vapor overhead 150 thermally couple the benzene column 110 and the cumene column 112. The side draw 144 and the vapor overhead 150 form a non-limiting embodiment of a thermal coupling 148 according to the present disclosure. The thermal coupling 148 is configured to provide heat transfer by direct contact, where a vapor stream is transferred in a direction opposite to a liquid stream between a specific location in each of the two columns 110, 112. For example, the specified location in the benzene column 110 may be the same stage of fractionating internals at which the side draw 144 is taken and the overhead vapor 150 is returned to the benzene column 110. Likewise, the specified location in the cumene column 112 may be the location, e.g., at or above the topmost fractionating internals, at which the side draw 144 is received in and the overhead vapor 150 is taken from the cumene column 112.

Figure 4:
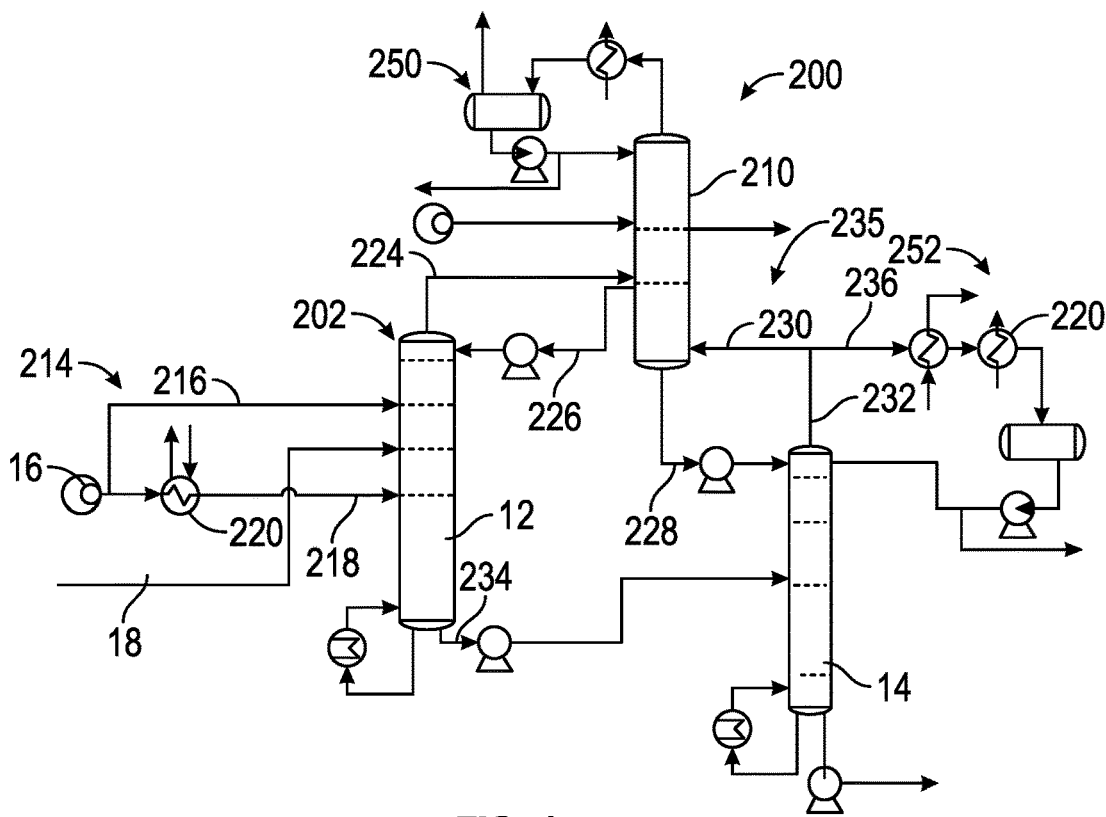
FIG. 4 depicts a retrofitted system for producing cumene according to one embodiment of the present disclosure.

Referring to FIG. 4, there is shown a cumene distillation system 200 that may be obtained by revamping a pre-existing conventional system 202. By "revamping," it is meant adding components and/or other structure to a pre-existing system that modify or otherwise alter the baseline performance, function, and/or efficiency of the pre-existing system. The conventional system 202 may include a pre-existing benzene column 12 and a pre-existing cumene column 14. The benzene column 12 receives a first feed 16 from an alkylation reactor and a second feed 18 from a transalkylation reactor. The term "pre-existing" means these components were present before a revamp activity. In some embodiments, the transalkylation reaction product feed 18 is fed into the benzene column 12 at a location between a first location at which the mostly liquid first portion 216 is fed into the benzene column 12 and a second location at which the at least partially vapor second portion 218 is fed into the benzene column 12.

In one non-limiting embodiment, a rectifier column 210 may be added to increase the number of fractionation stages in the system 200. Additional fractionation stages may be added by performing a retray on the cumene column 14 to increase the number of trays, e.g., a four for three retray. Since the overall configuration reduces the hydraulic loading on the cumene column 14, increasing the number of trays and reducing tray spacing will likely not sacrifice capacity. By "retray," is meant to replace the fractionating internals in the column 14, whether those fractionating internals are trays or packing. For simplicity, the discussion will refer to "trays."

To condition the first feed 16, the revamp adds a split-feed preheat assembly 214 to the benzene column 12. In the benzene column 12, a first portion 216 of the first feed 16 from alkylation reactor (not shown) enters the benzene column 12 at an upper feed location as liquid. A second portion 218 of the first feed 16 is partially vaporized in a feed heater 220 and enters the benzene column 12 as mostly a vapor at a feed location below the first portion 216. The feed heater 220 may receive thermal energy from a cumene effluent as described below or may receive thermal energy from another source.

The rectifier column 210 thermally couples the benzene column 12 with the cumene column 14. In one embodiment, the overhead vapor 224 from the benzene column 12, which is substantially free of DIPB, feeds to the revamp rectifier column 210, while a liquid draw 226 from the revamp rectifier column 210 serves as reflux for the benzene column 12. It should be noted that the overhead vapor 224 exits and the liquid draw 226 enters the benzene column 12 are both at least above the entry of the first feed portion 216. In examples, the overhead vapor 224 may exit and the liquid draw 226 may enter the benzene column 12 at the same location. The rectifier column 210 performs a separation between benzene and cumene. The liquid bottoms 228 from the rectifier column 210, which is substantially free of DIPB and benzene, feeds to the cumene column 14 as reflux. A first portion 230 of the overhead vapor 232 from the cumene column 12, which contains mostly cumene, returns to the bottom of the revamp rectifier column 210. A second portion 236 of the overhead vapor is used to provide feed preheat in the benzene column feed heater 220. The bottoms stream 234 from the benzene column 12 is substantially free of benzene and feeds to the cumene column 14 using existing equipment. The existing benzene column overhead condensing system 250 can be re-applied for the revamp rectifier column 210. The existing cumene column overhead condensing system 252 can be re-applied with some modifications. A second portion 236 of the overhead vapor is used to provide feed preheat in the benzene column feed heater 220. It should be noted that the two feed heaters 220 shown in FIG. 3 are the same feed heater. Thus, in the FIG. 4 embodiment, a thermal coupling 235 is formed by the rectifier column 210, the first portion 230 of the overhead vapor 232 returning to the rectifier column 210 from the cumene column 14, and the liquid bottoms 228 from the rectifier column 210 being fed as a reflux to the cumene column 14.

Hypothetical Example

Below is a table illustrating a predicted usages of HPS duty for a prior system represented by FIG. 1, a system according to the FIG. 3 embodiment, and a system according to the FIG. 4 embodiment. As shown below, the above-described systems are predicted to provide more than 30% reduction in reboiler heat requirements when compared to the benzene and cumene columns in conventional cumene distillation systems. And since these two columns typically represent approximately 90% of the total heat input to the cumene process, the present teachings may substantially improve the overall efficiency of the cumene process.

|  | UOM | Base (FIG. 1) | FIG. 3 | FIG. 4 |
| --- | --- | --- | --- | --- |
| Pressures | | | | |
| benzene Column - Ovhd Vapor | kg/cm2g | 0.4 | 0.4 | 0.5 |
| cumene Column - Ovhd Vapor | kg/cm2g | 0.4 | 0.55 | 0.6 |
| Revamp Rectifier - Ovhd Vapor | kg/cm2g | | | 0.4 |

-continued

| | UOM | Base (FIG. 1) | FIG. 3 | FIG. 4 |
|---|---|---|---|---|
| Temperatures | | | | |
| Split-feed heater outlet | C | | 156 | 160 |
| benzene Column - Bottom | C | 192 | 188 | 191 |
| benzene Column - Overhead Vapor | C | 92 | 83 | 121 |
| cumene Column - Bottom | C | 232 | 237 | 239 |
| cumene Column - Vapor Side Draw | C | | 171 | |
| cumene Column - Overhead Vapor | C | 164 | 130 | 171 |
| Revamp Rectifier - Bottom | C | | | 171 |
| Revamp Rectifier Ovhd Vapor | C | | | 87 |
| benzene Column number of (actual) trays | | 47 | 82 | 47 |
| cumene Column number of (actual) trays | | 46 | 83 | 61 |
| Revamp Rectifier number of (actual) trays | | | | 40 |
| benzene Feed Heater Duty | Gcal/h | | 3.00 | 3.28 |
| benzene Column Reboiler Duty, HPS | Gcal/h | 6.16 | 2.88 | 2.79 |
| cumene Column Reboiler Duty, HPS | Gcal/h | 7.68 | 6.65 | 6.44 |
| Total HPS Duty | Gcal/h | 13.84 | 9.53 | 9.24 |
| HPS Duty % of Base | | 100.0% | 68.9% | 66.7% |
| cumene Column (second) Condenser duty | Gcal/h | 8.09 | 2.75 | 2.40 |

From the above, it should be appreciated that what has been described includes a system for purifying cumene. The system may include a pre-existing benzene column and a pre-existing cumene column; a new retray assembly disposed in the pre-existing cumene column, wherein the new retray assembly has more trays than a pre-existing tray assembly in the pre-existing cumene column; and a new revamp rectifier column.

In some embodiments, the above described system for purifying cumene may include a new split feed assembly receiving a feed from an alkylation reactor, the split feed assembly including: a first feed line, a second feed line, and a heater, wherein a first feed portion enters the benzene column via the first feed line as a liquid, and a second feed portion enters the benzene column via the second feed line, and wherein the heater at least partially vaporizes the second feed portion before entering the benzene column.

In some embodiments, the above described system for purifying cumene may include a new first overhead draw line taking an overhead vapor from the benzene column at a first location and feeding the taken overhead vapor to the new revamp rectifier column; a new liquid draw line drawing a liquid from the revamp rectifier column at a location adjacent to the first location and feeding the drawn liquid to the benzene column; a new bottoms draw line drawing a liquid bottoms from the new revamp rectifier column and feeding to drawn liquid bottoms to the cumene column as reflux; and a new second overhead line receiving an overhead vapor from the pre-existing cumene column, the new second overhead line feeding a first a portion of the overhead vapor to a bottom of the new revamp rectifier column and feeding a second portion of the overhead vapor to the heater.

From the above, it should be appreciated that what has been described also includes a method for purifying cumene. In some embodiments, the method may include: adding a new split feed assembly to a pre-existing benzene column, the new split feed assembly including: a first feed line, a second feed line, and a heater; retraying a pre-existing cumene column using a new retray assembly, wherein the new retray assembly has more trays than a pre-existing tray assembly in the pre-existing cumene column; using the new split feed assembly to receive a feed from a pre-existing alkylation reactor, feeding a first feed portion to the pre-existing benzene column via the first feed line as a liquid; feeding a second feed portion to the pre-existing benzene column via the second feed line; and using the heater to partially vaporizes the second feed portion before the second feed portion enters the pre-existing benzene column.

In some embodiments, the above-described method for purifying cumene may include adding a new revamp rectifier column, adding a new first overhead draw line that connects the new revamp column to the pre-existing benzene column, adding a new first liquid draw line that connects the new revamp column to the pre-existing benzene column, adding a new bottoms draw line that connects the new revamp column to the pre-existing cumene column, and adding a new second overhead line that connects the pre-existing cumene column to the new revamp rectifier column; using the new first overhead draw line to take an overhead vapor from the pre-existing benzene column and feed the taken overhead vapor the new revamp rectifier column; using the new liquid draw line to take a liquid from the new revamp rectifier column at the same location as the new overhead draw line and feed the drawn liquid to the pre-existing benzene column; using the new bottoms draw line to take a liquid bottoms from the new revamp rectifier column and feed to taken liquid bottoms to the pre-existing cumene column as reflux; and using the new second overhead line to receive an overhead vapor from the pre-existing cumene column, the new second overhead line feeding a first a portion of the overhead vapor to a bottom of the new revamp rectifier column and feeding a second portion of the overhead vapor to the heater.

As used throughout, the terms "fractionation column" and "column" refer to any system, device, or combination of systems and/or devices suitable for the separation of a mixture containing two or more components having differing boiling points. Such fractionation columns or columns can include, but are not limited to, scrub columns, distillation columns, rectifier columns, and stripping columns.

As used throughout, the term "fractionating internals" includes, but is not limited to packing formed of material(s) that provide a large surface area per unit volume. The packing allows vapor and liquids to have continuous contact on the surfaces, which may be made of metal, ceramic, or plastic. "Fractionating internals" also include, but are not limited to, trays. Trays can include, but are not limited to, one or more types of trays that can improve the contact between gas and liquid phases within the fractionation column 110. Illustrative trays can include, but are not limited to perforated trays, sieve trays, bubble cap trays, floating valve trays, fixed valve trays, tunnel trays, cartridge trays, dual flow trays, baffle trays, shower deck trays, disc and donut trays, orbit trays, horse shoe trays, cartridge trays, snap-in valve trays, chimney trays, slit trays, or any combination thereof. As noted above, the term "retray" is used generically to refer to replacing any form of fractionating internals.

While the foregoing is directed to embodiments of the present invention, other and further embodiments of the invention may be devised without departing from the basic scope thereof, and the scope thereof is determined by the claims that follow.

What is claimed is:

1. A system for purifying cumene, the system comprising:
   a split feed assembly configured to receive an alkylation reaction product from an alkylation reactor, wherein the split feed assembly is configured to form the alkylation reaction product into a mostly liquid first stream and a second stream, and wherein the split feed assembly comprises a heater configured to at least partially vaporize the second stream to form an at least partially vapor second stream; and a benzene column configured to receive the mostly liquid first stream and the at least partially vapor second stream and to separate at least benzene from the mostly liquid first stream and the at least partially vapor second stream.

2. The system of claim 1, further comprising a transalkylation feed line configured to feed a transalkylation reaction product into the benzene column, wherein the transalkylation reaction product is fed into the benzene column at a location between a first location at which the mostly liquid first stream is fed into the benzene column and a second location at which the at least partially vapor second stream is fed into the benzene column.

3. The system of claim 1, further comprising:
a cumene column configured to form at least a purified cumene stream; and
a cumene draw line configured to direct the purified cumene stream from the cumene column to the heater, wherein the purified cumene stream is at least partially condensed in the heater.

4. The system of claim 3, wherein the cumene draw line is configured to form the purified cumene stream that has been at least partially condensed into a first portion and a second portion, wherein the first portion leaves as a purified cumene product and the second portion is returned to the cumene column at the same stage as the draw line.

5. The system of claim 1, further comprising:
a cumene column configured to form at least a purified cumene stream; and
a thermal coupling of the benzene column with the cumene column.

6. The system of claim 5, wherein the thermal coupling comprises a first side draw and an overhead line, wherein:
the first side draw is configured to draw a liquid substantially free of DIPB from the benzene column and direct the liquid drawn to the cumene column, the liquid drawn being a reflux to the cumene column; and
the overhead line configured to return a benzene enriched vapor from the cumene column to the benzene column, wherein the benzene enriched vapor has a higher concentration of benzene than the liquid drawn.

7. The system of claim 6, wherein the overhead line is configured to direct the benzene enriched vapor to a same stage as where the first side draw draws the liquid substantially free of DIPB.

8. A system for purifying cumene, comprising:
a benzene column and a cumene column;
a split feed assembly configured to receive an alkylation reaction product from an alkylation reactor, wherein the split feed assembly is configured to form the alkylation reaction product into a mostly liquid first stream and a second stream, wherein the split feed assembly comprises a heater configured to at least partially vaporize the second stream to form an at least partially vapor second stream, wherein the benzene column is configured to receive the mostly liquid first stream and the at least partially vapor second stream to separate at least benzene from the mostly liquid first stream and the at least partially vapor second stream;
a liquid side draw configured to direct a liquid substantially free of DIPB from the benzene column to the cumene column, the directed liquid being a reflux to the cumene column;
an overhead line from the cumene column configured to return a benzene enriched vapor to the benzene column, wherein the benzene enriched vapor has a higher concentration of benzene than the drawn liquid; and
a product side draw configured to draw the purified cumene from the cumene column.

9. The system of claim 8, further comprising an overhead draw line configured to take an overhead vapor from the cumene column and direct the taken over head vapor to a same fractionating internals location as the liquid side draw.

* * * * *